US012560579B2

(12) United States Patent
Tripathy et al.

(10) Patent No.: US 12,560,579 B2
(45) Date of Patent: Feb. 24, 2026

(54) METHODS, APPARATUSES, AND COMPUTER PROGRAM PRODUCTS FOR BLOCKAGE DETECTION IN POROUS MEDIA

(71) Applicant: Honeywell Analytics Inc., Charlotte, NC (US)

(72) Inventors: Janmejaya Tripathy, Charlotte, NC (US); Sumit Suresh Kulkarni, Charlotte, NC (US); Renuka Prasad G, Charlotte, NC (US)

(73) Assignee: Honeywell Analytics Inc., Charlotte, NC (US)

( * ) Notice: Subject to any disclaimer, the term of this patent is extended or adjusted under 35 U.S.C. 154(b) by 286 days.

(21) Appl. No.: 18/521,499

(22) Filed: Nov. 28, 2023

(65) Prior Publication Data

US 2024/0192173 A1     Jun. 13, 2024

(30) Foreign Application Priority Data

Dec. 12, 2022     (IN) .............................. 202211071610

(51) Int. Cl.
*G01N 29/036*          (2006.01)
*G01N 33/00*          (2006.01)

(52) U.S. Cl.
CPC ....... *G01N 29/036* (2013.01); *G01N 33/0027* (2013.01); *G01N 2291/021* (2013.01)

(58) Field of Classification Search
CPC ................................................... G01N 29/036

(Continued)

(56) References Cited

U.S. PATENT DOCUMENTS 4,175,242 A     11/1979   Kleinschmidt
6,443,010 B1     9/2002   Scofield
(Continued)

FOREIGN PATENT DOCUMENTS

JP          2008-017261 A     1/2008

OTHER PUBLICATIONS

Mitri, Farid G. "Inverse determination of porosity from objectas resonances." Journal of applied physics 96.10 (2004): 5866-5869. (Year: 2004).*

(Continued)

*Primary Examiner* — Walter L Lindsay, Jr.
*Assistant Examiner* — Philip T Fadul
(74) *Attorney, Agent, or Firm* — Alston & Bird LLP

(57)          ABSTRACT

Methods, apparatuses, and computer program products for monitoring environmental conditions are provided. For example, a computer-implemented method may include transmitting a plurality of signals to a vibration actuator coupled to a resonator that is affixed to a porous media of a diffusion sensor, each of the plurality of signals causing the vibration actuator and the coupled resonator to vibrate at a corresponding different one of a plurality of frequencies; detecting a plurality of vibration displacements of the resonator, each of the plurality of vibration displacements corresponding to a different one of the plurality of frequencies; determining a maximum vibration displacement of the resonator and an associated one of the plurality of frequencies at which the maximum vibration displacement occurs, thereby determining a resonant frequency of the porous media; and periodically determining if the resonant frequency of the porous media has changed.

20 Claims, 6 Drawing Sheets

(58) Field of Classification Search
USPC ........................................................ 73/24.06
See application file for complete search history.

(56) References Cited

U.S. PATENT DOCUMENTS

| | | | |
|---|---|---|---|
| 8,898,874 | B2 | 12/2014 | Tomiyama et al. |
| 11,415,562 | B2 | 8/2022 | Sexton et al. |
| 2011/0072886 | A1 | 3/2011 | Caneau et al. |
| 2016/0334317 | A1 | 11/2016 | Killard et al. |
| 2017/0234741 | A1* | 8/2017 | Erickson .................. G01K 7/36 |
| | | | 374/188 |
| 2020/0363306 | A1 | 11/2020 | Sexton et al. |

OTHER PUBLICATIONS automation.com, "Breakthrough Diffusion Supervision Technology Sets New Standard for Fixed Gas Detection Reliability and Safety", retrieved from the Internet at URL: <https://www.automation.com/en-us/products/product01/breakthrough-diffusion-supervision-technology-sets> on Mar. 25, 2024, 2 pages.

Ji-Seob Choi et al., "MEMS particle sensor based on resonant frequency shifting," Micro and Nano System Letters, 8(17):1-6, (2020). [Retrieved from the Internet Mar. 25, 2024: URL: <https://mnsl-journal.springeropen.com/articles/10.1186/s40486-020-00118-9>].

Nelson Aguilar, "Use a Low-Frequency Sound to Get Water Out of Your iPhone," CNET, 8 pages, (Jul. 14, 2022). [Retrieved from the Internet Mar. 25, 2024: URL: <https://www.cnet.com/tech/mobile/use-a-low-frequency-sound-to-get-water-out-of-your-iphone/>].

Communication about intention to grant a European patent Mailed on Mar. 27, 2025 for EP Application No. 23208713, 6 page(s).

A. Hasani Baferani et al., "Toward mechanistic understanding of the relationship between the sound absorption and the natural and resonant frequencies of porous media," The Journal of the Acoustical Society of America, 140(6):4246-4259, (Dec. 15, 2016).

Extended European Search Report Mailed on Apr. 22, 2024 for EP Application No. 23208713, 12 page(s).

Farid G. Mitri, "Inverse determination of porosity from object's resonances," Journal of Applied Physics, 96(10):5866-5869, (Nov. 15, 2004).

* cited by examiner

100

120

105

250

O2

20.9

115

110

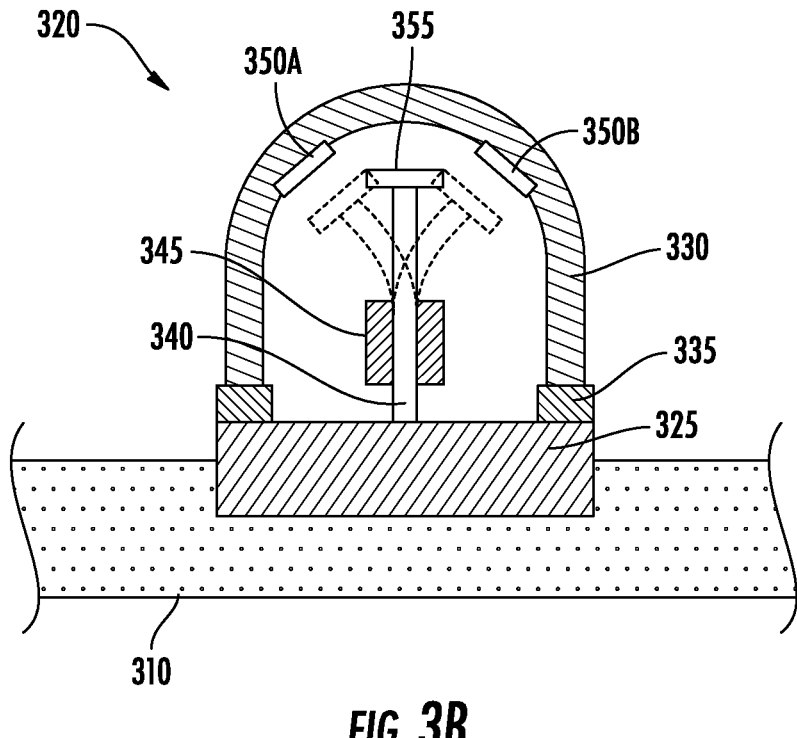
FIG. *3B*

400

A

DETECT DISPLACEMENT OF TUNING
FORK AT EACH FREQUENCY     440

DETERMINE MAX DISPLACEMENT AND
ASSOCIATED (NEW) RESONANT FREQUENCY     445

VIBRATE TUNING FORK AT NEW RESONANT
FREQUENCY FOR CLEANING     450

VIBRATE TUNING FORK AT CALIBRATED FREQUENCY
AND DETECT DISPLACEMENT     455

460

DISPLACEMENT = MAX
(W/IN TOLERANCE)?     YES     B

NO

ALERT FOR MANUAL
CLEANING / REPLACEMENT     465

START     470

METHODS, APPARATUSES, AND COMPUTER PROGRAM PRODUCTS FOR BLOCKAGE DETECTION IN POROUS MEDIA

CROSS-REFERENCE TO RELATED APPLICATIONS

This application claims priority pursuant to 35 U.S.C. 119(a) to Indian Application No. 202211071610, filed Dec. 12, 2022, which application is incorporated herein by reference in its entirety.

FIELD OF THE INVENTION

Example embodiments of the present disclosure relate generally to diffusion sensors and, more particularly, to methods, apparatuses, and computer program products for blockage detection in porous media of diffusion sensors.

BACKGROUND

Gas sensors (also termed gas detectors or gas monitors) are used in many industrial workplaces to detect the presence of hazardous or potentially hazardous gases in the atmosphere, which may include flammable or toxic gases. Such gas sensors may be configured to detect one or more gases, such as methane, propane, carbon dioxide, carbon monoxide, hydrogen sulfide, nitrogen dioxide, hydrogen, or oxygen. Such gas sensors may use several different sensor technologies, including electrochemical, infrared, and catalytic bead.

Such gas sensors are typically classified as either diffusion sensors or sampling sensors. A diffusion gas sensor is used by bringing it into areas where gas may be a problem. A diffusion sensor relies on the principle of the "spreading out" of molecules and gases in the atmosphere. As these gases spread and expand, higher and lower concentrations of certain gases are able to be identified. The sensors need to physically come into contact with the gas it is designed to monitor. Sampling gas sensors have pumps designed to pull air from a remote location (often a confined space) to detect the presence of hazardous or potentially hazardous gases in the space.

Diffusion gas sensors are typically installed in an enclosure. The enclosure has an opening through which the air and any hazardous or potentially hazardous gases diffuse to reach the sensor. The enclosure opening is often spanned by a porous media, such as a porous frit made of metal or glass. The porous media helps to diffuse air towards the sensor, while also protecting the sensor from potential contaminants, such as dust and insects. However, such contaminants may become attached to the outer surface of the porous media and/or lodged in its pores, thereby partially or completely blocking the porous media. Such a partial or complete blockage of the porous media reduces or eliminates air diffusion to the sensor and may therefore prevent the sensor from detecting its target hazardous or potentially hazardous gas. Additionally, such a partial or complete blockage is difficult, if not impossible, to detect without manually inspecting the porous media.

Through applied effort, ingenuity, and innovation, many of these identified problems have been solved by developing solutions that are included in embodiments of the present disclosure, many examples of which are described in detail herein.

BRIEF SUMMARY

Various embodiments described herein relate to methods, apparatuses, and computer program products for blockage detection in porous media.

In accordance with various embodiments of the present disclosure, an apparatus is provided. In some embodiments, the apparatus comprises at least one processor and at least one non-transitory memory comprising program code. In some embodiments, the at least one non-transitory memory and the program code are configured to, with the at least one processor, cause the apparatus to at least: transmit a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies; detect a plurality of vibration displacements of the resonator, each of the plurality of vibration displacements corresponding to a different one of the plurality of frequencies; from the plurality of vibration displacements, determine a maximum vibration displacement of the resonator and an associated one of the plurality of frequencies at which the maximum vibration displacement occurs, thereby determining a resonant frequency of the porous media; and periodically determine if the resonant frequency of the porous media has changed by: transmitting a resonance signal to the vibration actuator to cause the vibration actuator, and therefore the coupled resonator, to vibrate at the determined resonant frequency of the porous media; detecting a verification vibration displacement of the resonator; and determining if the verification vibration displacement of the resonator is within a predetermined range of the maximum vibration displacement of the resonator.

In some embodiments, the vibration actuator comprises a piezoelectric actuator or an electromagnetic actuator.

In some embodiments, the resonator comprises one of a tuning prong or a tuning fork.

In some embodiments, the porous media comprises porous frit.

In some embodiments, the plurality of signals transmitted to the vibration actuator is a first plurality of signals; the plurality of vibration displacements is a first plurality of vibration displacements; the plurality of frequencies is a first plurality of frequencies; the resonant frequency of the porous media is a first resonant frequency; the resonance signal is a first resonance signal; and the maximum vibration displacement is a first maximum vibration displacement. If the verification vibration displacement of the resonator is determined to not be within the predetermined range of the first maximum vibration displacement of the resonator, the at least one non-transitory memory and the program code are configured to, with the at least one processor, cause the apparatus to: transmit a second plurality of signals to the vibration actuator, each of the second plurality of signals causing the vibration actuator, and therefore the coupled resonator, to vibrate at a corresponding different one of a second plurality of frequencies; detect a second plurality of vibration displacements of the resonator, each of the second plurality of vibration displacements corresponding to a different one of the second plurality of frequencies; from the second plurality of vibration displacements, determine a second maximum vibration displacement of the resonator and an associated one of the second plurality of frequencies at which the second maximum vibration displacement occurs, thereby determining a second resonant frequency of the porous media; and transmit a second resonance signal to the vibration actuator to cause the vibration actuator, and therefore the coupled resonator, to vibrate at the second resonant frequency for a predetermined amount of time to attempt to dislodge any foreign matter on or in the porous media.

In some embodiments, transmitting the second resonance signal to the vibration actuator causes the vibration actuator, and therefore the coupled resonator, to vibrate at a higher magnitude than the vibrations caused by the first plurality of signals, the second plurality of signals, or the first resonance signal.

In some embodiments, the verification vibration displacement is a first verification vibration displacement, after transmitting the second resonance signal to the vibration actuator to cause the vibration actuator, and therefore the coupled resonator, to vibrate at the second resonant frequency for the predetermined amount of time, the at least one non-transitory memory and the program code are configured to, with the at least one processor, cause the apparatus to: transmit the first resonance signal to the vibration actuator to cause the vibration actuator, and therefore the coupled resonator, to vibrate at the first resonant frequency of the porous media; detect a second verification vibration displacement of the resonator; and determine if the second verification vibration displacement of the resonator is within the predetermined range of the first maximum vibration displacement of the resonator. If the second verification vibration displacement of the resonator is determined to not be within the predetermined range of the first maximum displacement of the resonator, the at least one non-transitory memory and the program code are configured to, with the at least one processor, cause the apparatus to provide an alert that manual clearing or replacement of the porous media is needed.

In accordance with various embodiments of the present disclosure, a computer-implemented method is provided. In some embodiments, the computer-implemented method comprises transmitting a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies; detecting a plurality of vibration displacements of the resonator, each of the plurality of vibration displacements corresponding to a different one of the plurality of frequencies; from the plurality of vibration displacements, determining a maximum vibration displacement of the resonator and an associated one of the plurality of frequencies at which the maximum vibration displacement occurs, thereby determining a resonant frequency of the porous media; and periodically determining if the resonant frequency of the porous media has changed by: transmitting a resonance signal to the vibration actuator to cause the vibration actuator, and therefore the coupled resonator, to vibrate at the determined resonant frequency of the porous media; detecting a verification vibration displacement of the resonator; and determining if the verification vibration displacement of the resonator is within a predetermined range of the maximum vibration displacement of the resonator.

In accordance with various embodiments of the present disclosure, a computer program product is provided. In some embodiments, the computer program product comprises at least one non-transitory computer-readable storage medium having computer-readable program code portions stored therein. In some embodiments, the computer-readable program code portions comprise an executable portion configured to transmit a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies; detect a plurality of vibration displacements of the resonator, each of the plurality of vibration displacements corresponding to a different one of the plurality of frequencies; from the plurality of vibration displacements, determine a maximum vibration displacement of the resonator and an associated one of the plurality of frequencies at which the maximum vibration displacement occurs, thereby determining a resonant frequency of the porous media; and periodically determine if the resonant frequency of the porous media has changed by: transmitting a resonance signal to the vibration actuator to cause the vibration actuator, and therefore the coupled resonator, to vibrate at the determined resonant frequency of the porous media; detecting a verification vibration displacement of the resonator; and determining if the verification vibration displacement of the resonator is within a predetermined range of the maximum vibration displacement of the resonator.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which:

FIG. 3B is a close-up view of a portion of the sectional view of FIG. 3A;

DETAILED DESCRIPTION OF THE INVENTION

Figure 1:
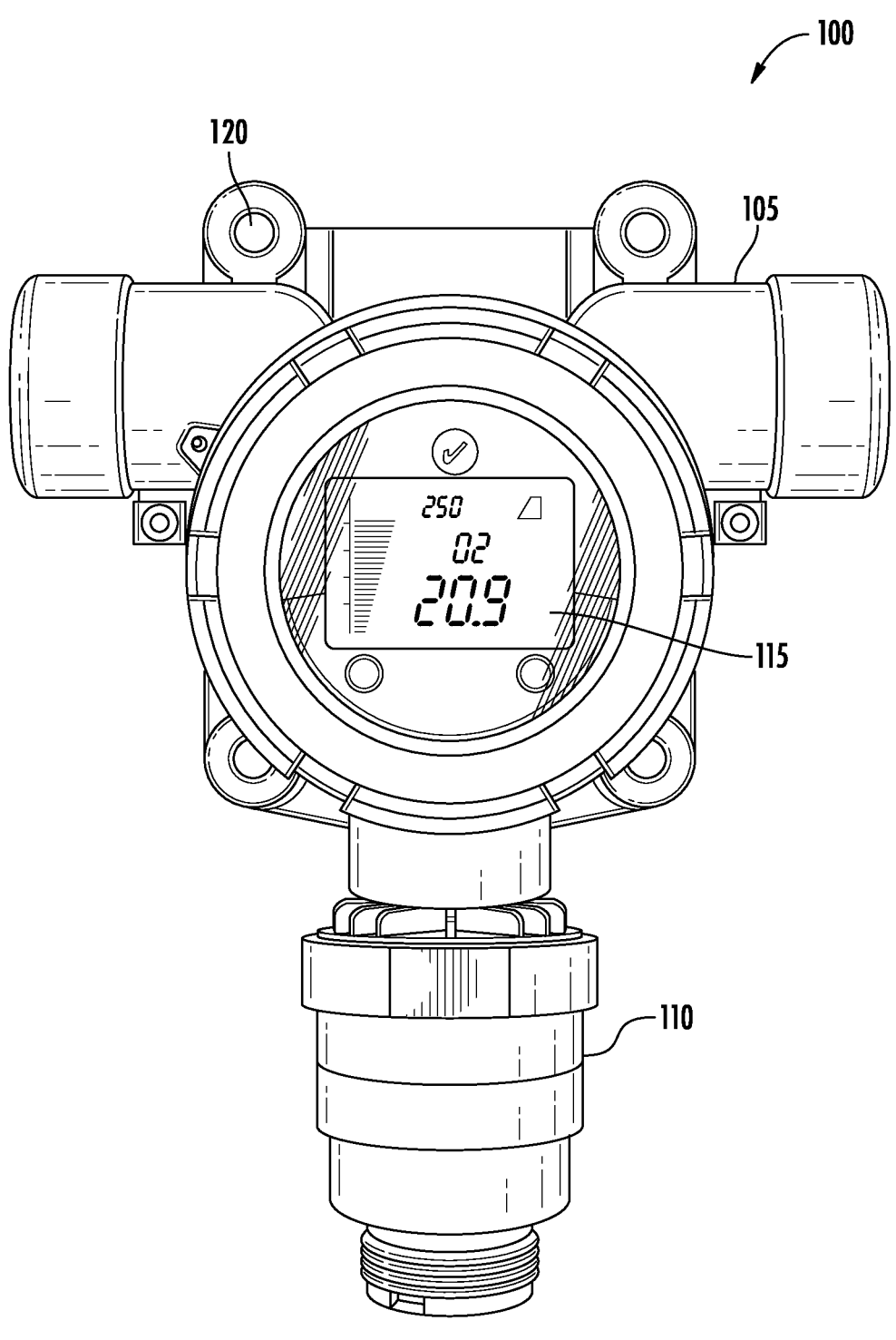
FIG. 1 is a front view of an example diffusion gas sensor in accordance with example embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear." "top." etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," "in some embodiments." and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could." "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

The term "electronically coupled," "electronically coupling," "electronically couple," "in communication with," "in electronic communication with," or "connected" in the present disclosure refers to two or more elements or components being connected through wired means and/or wireless means, such that signals, electrical voltage/current, data and/or information may be transmitted to and/or received from these elements or components.

Various embodiments of the present disclosure provide apparatuses, methods, and computer program products that detect a blockage, partial blockage, or potential blockage in porous media, such as the porous media of a diffusion gas sensor, by detecting a change in the resonant frequency of the porous media. As contaminants become attached to the outer surface of the porous media and/or lodged in its pores, the mass of the porous media increases. The increased mass of the porous media changes its resonant frequency. By detecting this change in the resonant frequency, various embodiments of the present disclosure are thereby able to detect a blockage, partial blockage, or potential blockage in the porous media.

In example embodiments, a microelectromechanical systems (MEMS) device is affixed to the porous media. The MEMS device enables determination of the resonant frequency of the porous media before the porous media has been used, such that the porous media is clear/unblocked. This process may be termed calibration or detection of the baseline resonant frequency. The MEMS device then enables periodic determination of the resonant frequency of the porous media after use has begun. By detecting a change in the resonant frequency of the porous media, it is known that contaminants have become attached to the outer surface of the porous media and/or lodged in its pores and it can be inferred that some blockage is present. The more contaminants that have become attached to the outer surface of the porous media, the greater the change in the resonant frequency of the porous media and therefore (it can be inferred), the greater the amount of blockage that is present.

Because the device affixed to the porous media is a MEMS device, the device is therefore small enough that the device does not negatively affect the diffusion of gas through the porous media. In some embodiments, the device is less than about one cubic centimeter.

Referring now to the figures, FIG. 1 is a front view of an example diffusion gas sensor in accordance with example embodiments of the present disclosure. FIG. 1 shows an example diffusion gas sensor 100 having an upper housing 105 and a lower housing 110. The upper housing 105 typically houses a display 115, a power supply, and control electronics, and has mounting holes 120 or the like for mounting the device. The lower housing 110 typically houses the sensor component and has an open lower end into which air diffuses. The open lower end of the lower housing 110 is spanned or capped by the porous media (as shown in FIG. 3).

Figure 2:
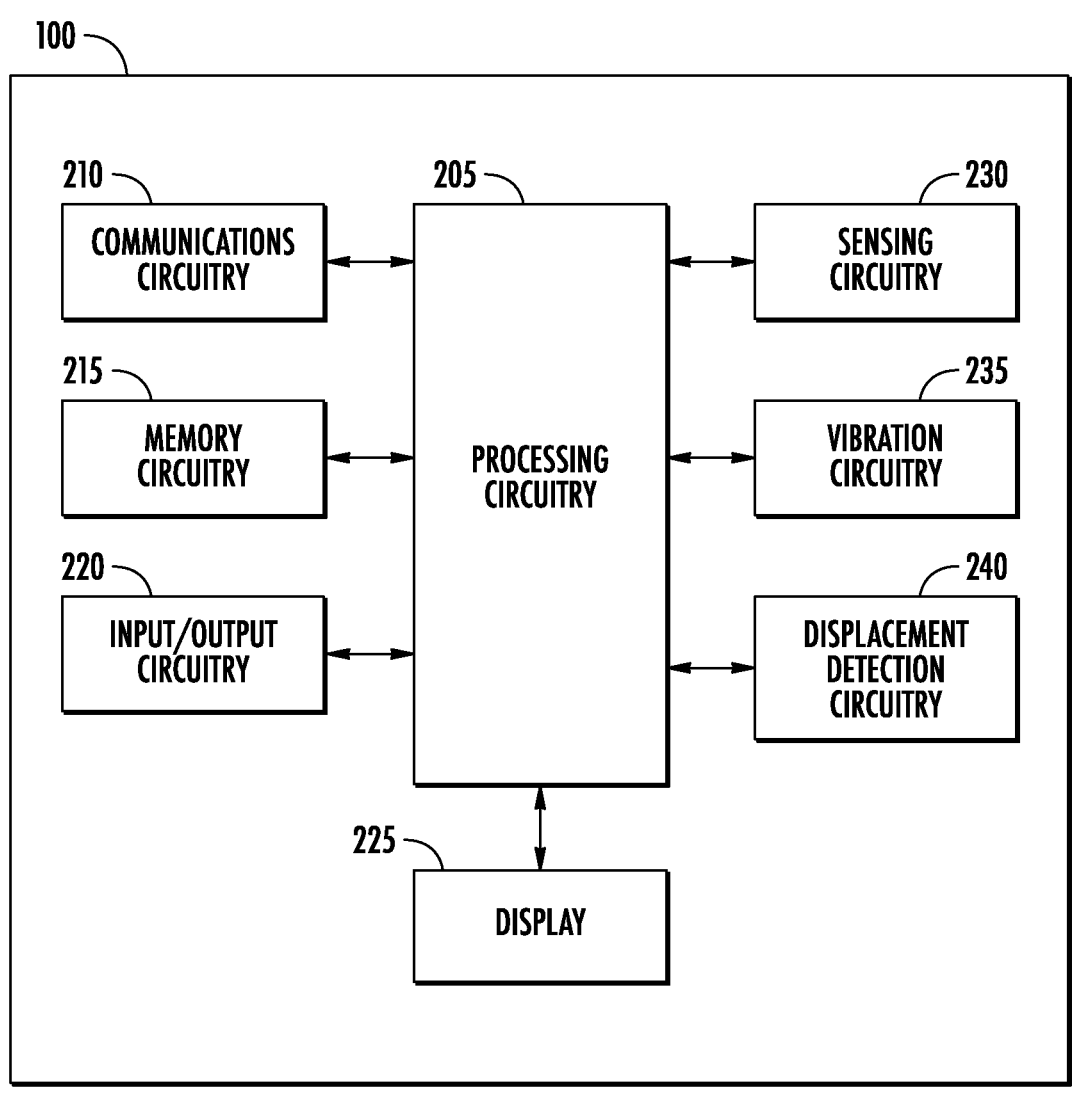
FIG. 2 illustrates an example block diagram of an example gas diffusion sensor in accordance with example embodiments of the present disclosure.

FIG. 2 is an example block diagram of an example gas diffusion sensor in accordance with example embodiments of the present disclosure. FIG. 2 illustrates an example gas diffusion sensor 100 that can detect a blockage (or potential blockage) in porous media, such as the porous media of a diffusion gas sensor, by detecting a change in the resonant frequency of the porous media. In the illustrated embodiment, the gas diffusion sensor 100 comprises processing circuitry 205, communications circuitry 210, memory circuitry 215, input/output circuitry 220, a display 225, sensing circuitry 230, vibration circuitry 235, and displacement detection circuitry 240.

In an example embodiment, the processing circuitry 205 controls the operation of the gas diffusion sensor 100 and its various components, typically according to configuration data and instructional programming stored in the memory circuitry 215. The processing circuitry 205 can detect one or more hazardous or potentially hazardous gases, such as via sensing circuitry 230. The processing circuitry 205 can determine the resonance frequency of the porous media, such as via the vibration circuitry 235 and the displacement detection circuitry 240 (as described in detail below). In some embodiments, the vibration circuitry 235 imparts a vibration to the porous media and the displacement detection circuitry 240 measures the magnitude of the vibration (which will be greatest at the resonant frequency of the porous media). As described further below, in some embodiments the vibration circuitry comprises a vibration actuator and a resonator.

In some embodiments, the communications circuitry 210 enables the gas diffusion sensor 100 to communicate with a central monitoring device (not illustrated) to transmit information about the status of the gas diffusion sensor 100. For example, the gas diffusion sensor 100 may transmit information about detected hazardous gas and/or information about a potential blockage of the porous media.

In some embodiments, the input/output circuitry 220 enables a user to interface with gas diffusion sensor 100, such as by initiating a resonant frequency calibration routine when a new porous media is installed.

In some embodiments, the gas diffusion sensor 100 may display information for a user via the display 225. Such displayed information may include, for example, a level of a hazardous or potentially hazardous gas detected. In various examples of the present disclosure, the display 325 may include a liquid crystal display (LCD), a light-emitting diode (LED) display, a plasma (PDP) display, a quantum dot (QLED) display, and/or the like. Additionally or alternatively, in various examples of the present disclosure, such information and/or alerts related to hazardous or potentially hazardous gases detected may be transmitted to one or more user communications devices (e.g., mobile phone or the like) for a user to view, such as via communications circuitry 210.

The gas diffusion sensor 100 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitries may both leverage use of the same processor, network interface, storage medium, or the like to perform their associated functions, such that duplicate hardware is not required for each set of circuitries.

The use of the term "circuitry" as used herein with respect to components of the apparatus should therefore be understood to include particular hardware configured to perform the functions associated with the particular circuitry as described herein. The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the gas diffusion sensor 100 may provide or supplement the functionality of particular circuitry. For example, the processing circuitry 205 may provide processing functionality, the communications circuitry 210 may provide network interface functionality, the memory circuitry 215 may provide storage functionality, and the like.

In some embodiments, the processing circuitry 205 (and/or co-processor or any other processing circuitry assisting or otherwise associated with the processor) may be in communication with the memory circuitry 215 via a bus for passing information among components of the apparatus. The processing circuitry 205 may be embodied in a number of different ways and may, for example, include one or more processing devices configured to perform independently. Additionally, or alternatively, the processing circuitry 205 may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

For example, the processing circuitry 205 may be embodied as one or more complex programmable logic devices (CPLDs), microprocessors, multi-core processors, co-processing entities, application-specific instruction-set processors (ASIPs), and/or controllers. Further, the processing circuitry 205 may be embodied as one or more other processing devices or circuitry. The term circuitry may refer to an entirely hardware embodiment or a combination of hardware and computer program products. Thus, the processing circuitry 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing circuitry 205 may be configured for a particular use or configured to execute instructions stored in volatile or non-volatile media or otherwise accessible to the processing circuitry 205. As such, whether configured by hardware or computer program products, or by a combination thereof, the processing circuitry 205 may be capable of performing steps or operations according to embodiments of the present disclosure when configured accordingly.

In an example embodiment, the processing circuitry 205 may be configured to execute instructions stored in the memory circuitry 215 or otherwise accessible to the processor. Alternatively, or additionally, the processing circuitry 205 may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processing circuitry 205 is embodied as an executor of software instructions, the instructions may specifically configure the processor to perform the algorithms and/or operations described herein when the instructions are executed.

In some embodiments, the memory circuitry 215 may further include or be in communication with volatile media (also referred to as volatile storage, memory, memory storage, memory circuitry and/or similar terms used herein interchangeably). In some embodiments, the volatile storage or memory may also include, such as but not limited to, RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the memory circuitry 215 may be used to store at least portions of the databases, database instances, database management system entities, data, applications, programs, program modules, scripts, source code, object code, byte code, compiled code, interpreted code, machine code, executable instructions, and/or the like being executed by, for example, the processing circuitry 205 as shown in FIG. 2. Thus, the databases, database instances, database management system entities, data, applications, programs, program modules, scripts, source code, object code, byte code, compiled code, interpreted code, machine code, executable instructions, and/or the like may be used to control certain aspects of the operation of the gas diffusion sensor 100 with the assistance of the processing circuitry 205 and operating system.

In some embodiments, the memory circuitry 215 may further include or be in communication with non-volatile media (also referred to as non-volatile storage, memory, memory storage, memory circuitry and/or similar terms used herein interchangeably). In some embodiments, the memory circuitry 215 may include, such as, but not limited to, hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the memory circuitry 215 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to may refer to a structured or unstructured collection of information/data that is stored in a computer-readable storage medium.

In various embodiments of the present disclosure, the memory circuitry 215 may also be embodied as a data storage device or devices, as a separate database server or servers, or as a combination of data storage devices and separate database servers. Further, in some embodiments, memory circuitry 215 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery system may be stored. Further, the information/data required for the operation of the recovery system may also be partially stored in the cloud data storage system and partially stored in a locally maintained data storage system. More specifically, memory circuitry 215 may encompass one or more data stores configured to store information/data usable in certain embodiments.

In the example as shown in FIG. 2, one or more instances of circuitry may be part of the memory circuitry 215. In this example, the term "circuitry" refers to one or more data storage units in the memory circuitry 215 that may store executable computer program instructions. When the executable computer program instructions stored in such circuitry are executed by a processing circuitry (such as, but not limited to, the processing circuitry 205 shown in FIG. 2), the executable computer program instructions may cause the processing circuitry to perform one or more functions.

The communications circuitry 210 may be any means such as a device or circuitry embodied in either hardware or a combination of hardware and software that is configured to receive and/or transmit data from/to a network and/or any other device, circuitry, or module in communication with the gas diffusion sensor 100. In this regard, the communications circuitry 210 may include, for example, a network interface for enabling communications with a wired or wireless communication network and/or in accordance with a variety of networking protocols described herein. For example, the communications circuitry 210 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s).

It is also noted that all or some of the information discussed herein can be based on data that is received, generated and/or maintained by one or more components of the gas diffusion sensor 100. In some embodiments, one or more external systems (such as a remote cloud computing and/or data storage system) may also be leveraged to provide at least some of the functionality discussed herein.

In some embodiments, the input/output circuitry 220 may be in communication with, respectively, the processing circuitry 205 to provide output to the user and, in some embodiments, to receive an indication of a user input. The input/output circuitry 220 may include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., the memory circuitry 215, and/or the like).

Figure 3A:
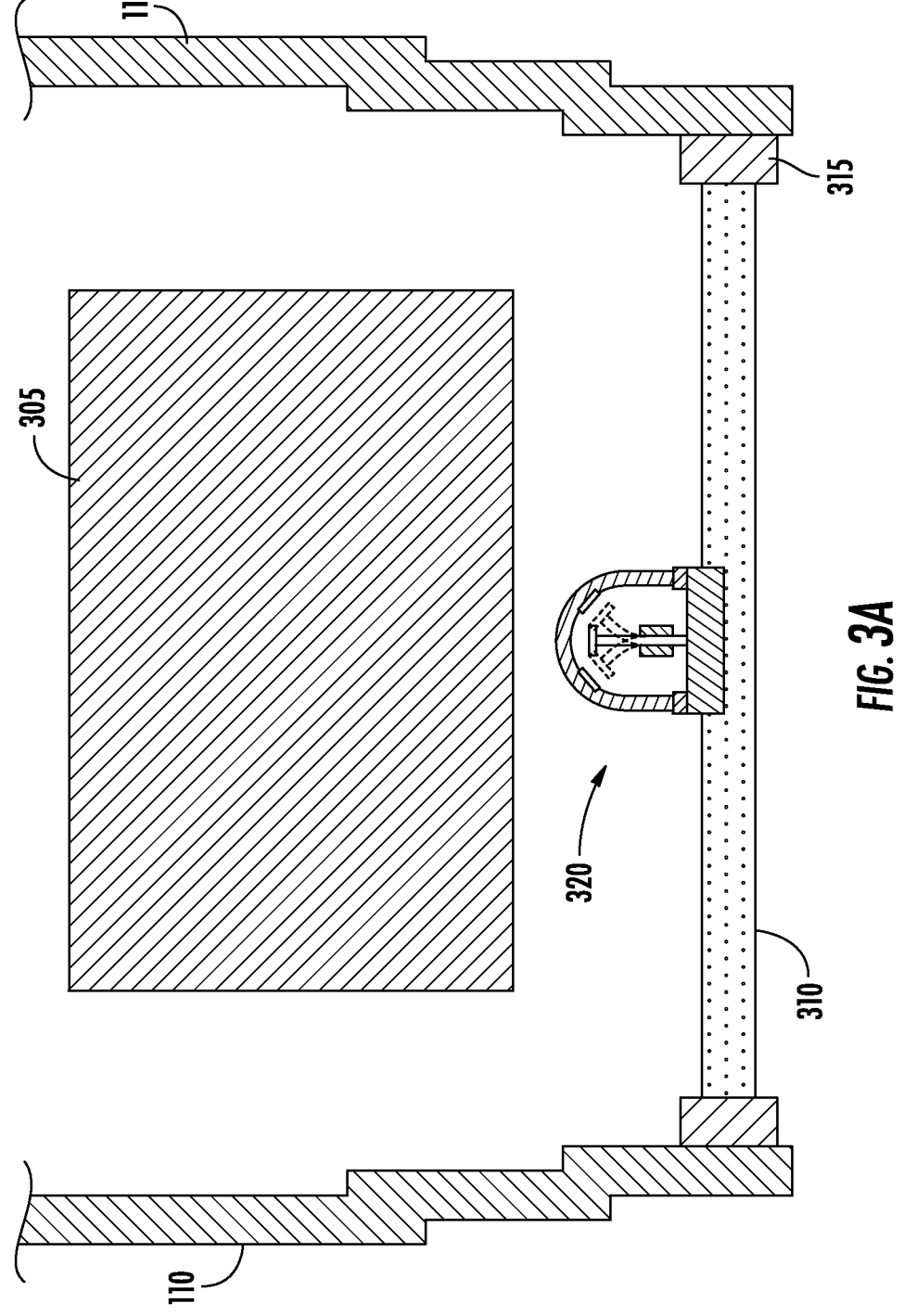
FIG. 3A is a sectional view of a portion of an example gas diffusion sensor in accordance with example embodiments of the present disclosure.

Reference will now be made to FIGS. 3A and 3B, which provide sectional views of a portion of an example gas diffusion sensor in accordance with example embodiments of the present disclosure. FIGS. 3A and 3B show sectional views of the lower housing 110 of the gas diffusion sensor 100. In some embodiments, such as is shown in the section view of the example embodiment of FIGS. 3A and 3B, a sensing component 305 is located within the lower housing 110. In some embodiments, various types of sensing components may be installed, depending on the desired gas(es) to be detected. A porous media 310 (which may be any suitable type of porous media, for example, a porous frit made of glass or metal) spans the lower opening of the lower housing 110 and is held in place by a circumferential packing/isolation ring 315. A MEMS vibration/detection device 320 has a base 325 that is affixed to the porous media. In some embodiments, the base 325 of the vibration/detection device 320 is affixed to the porous media 310 using any suitable mechanism or method of affixation, including but not limited to any suitable adhesive (preferably an adhesive that produces little or no vibration damping) or swaging.

In some embodiments, a shielding enclosure 330 is attached to the base 325, such as by an isolation ring 335, and houses/protects the internal components of the vibration/detection device 320. In some embodiments, the enclosure 330 and the base 325 are constructed of stainless steel, aluminum, or any other suitable material. In some embodiments, the isolation ring 335 is constructed of silicone or any other suitable material.

In some embodiments, within the enclosure 330 are components for imparting a vibration into the porous media and detecting the vibration displacement to determine the resonant frequency of the porous media. In some embodiments, such as is shown in the example embodiment of FIGS. 3A and 3B, a resonator 340 is affixed to the base 325 and a vibration actuator 345 is coupled to the resonator 340. The resonator may comprise any suitable type of mechanical resonator. In some embodiments, the resonator comprises a tuning fork or a tuning prong. The vibration actuator may comprise any suitable device capable of imparting vibrations at a plurality of desired frequencies to the porous media. The vibration actuator may be internal (i.e., on the inner side of the porous media or external (i.e., on the outer side of the porous media). In some embodiments, the vibration actuator comprises a piezoelectric actuator. In some alternative embodiments, the vibration actuator comprises an electromagnetic actuator. When an electrical signal is provided to the vibration actuator 345, the vibration actuator 345 vibrates according to the frequency of the electrical signal. The vibration of the vibration actuator 345 imparts a corresponding vibration to the resonator 340, which in turn imparts a corresponding vibration to the porous media 310. The magnitude of the vibrations can be measured by measuring the back-and-forth motion (illustrated by the dashed lines in FIGS. 3A and 3B) of the upper end(s) of the resonator 340.

Any suitable mechanism/method may be used to measure the movement of the resonator and therefore the magnitude of the vibrations. In some embodiments, such as is shown in the example embodiment of FIGS. 3A and 3B, a conductive plate 355 sits atop the upper end(s) of the resonator and either one or two (two are shown) fixed-position electrodes 350A, 350B are affixed to the inside surface of the upper portion of the enclosure 330. (The conductive plate 355 is essentially an electrode, but the term "conductive plate" is used herein to distinguish the conductive plate 355 from the electrodes 350A, 350B.) In some embodiments, the conductive plate is an integral part of the resonator, while in some embodiments the conductive plate is a separate component that has been affixed to the upper end of the resonator. In some embodiments, the back-and-forth movement of the resonator and therefore the magnitude of the vibrations is measured by measuring the capacitance between each electrode 350A, 350B and the conductive plate 355 while the resonator is vibrating. Capacitance is directly proportional to the electrostatic force field between two plates (such as between the conductive plate 355 and the first electrode 350A or between the conductive plate 355 and the second electrode 350B)—as the distance between the plates decreases, capacitance increases. In some embodiments, the electrodes 350A, 350B are positioned such that the distance between each electrode 350A, 350B and the conductive plate 355 is the least (and therefore the capacitance is the greatest) at the expected maximum displacement of the resonator 340.

FIGS. 3A and 3B illustrate the use of two electrodes 350A, 350B. The use of two electrodes provides two vibration displacement measurements which can be compared for verification. If a difference is detected at a particular frequency between the vibration displacement measurements from the two electrodes, in some embodiments the larger or smaller of the two measurements is used. Alternatively, in some embodiments, if a difference is detected at a particular frequency between the vibration displacement measurements from the two electrodes, multiple measurements from each of the electrodes may be averaged. In some embodiments, only one electrode is used.

Figure 4A:
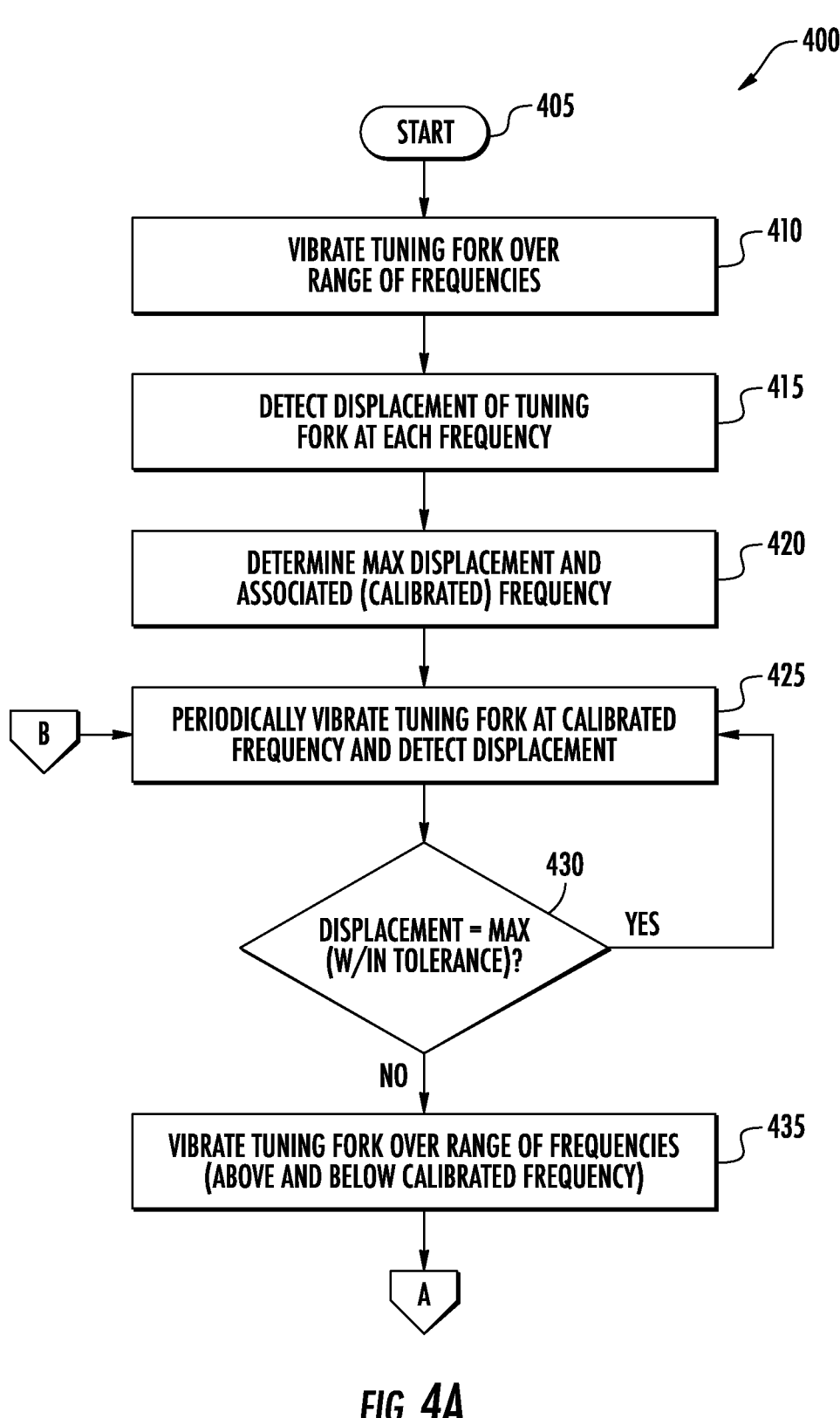
FIGS. 4A and 4B are an example flowchart illustrating an example method for detecting a blockage in porous media of an example gas diffusion sensor in accordance with example embodiments of the present disclosure.
Figure 4B:
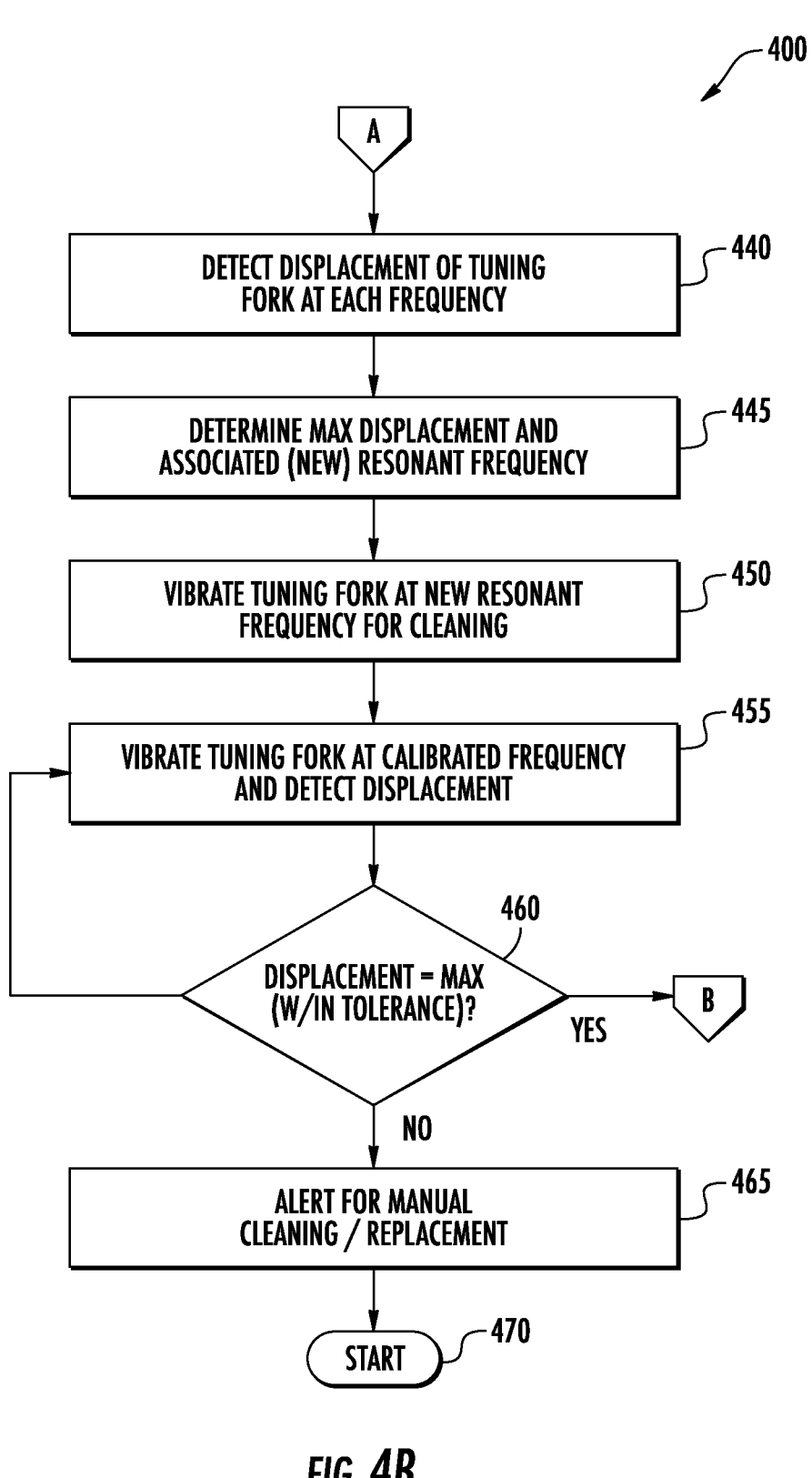

Reference will now be made to FIGS. 4A and 4B, which provides a flowchart illustrating example steps, processes, procedures, and/or operations in accordance with various embodiments of the present disclosure. Various methods described herein, including, for example, example methods as shown in FIGS. 4A and 4B, may provide various technical benefits and improvements. It is noted that each block of the flowchart, and combinations of blocks in the flowchart, may be implemented by various means such as hardware, firmware, circuitry and/or other devices associated with execution of software including one or more computer program instructions. For example, one or more of the procedures described in FIGS. 4A and 4B may be embodied by computer program instructions, which may be stored by a non-transitory memory of an apparatus employing an embodiment of the present disclosure and executed by a processor in the apparatus. These computer program instructions may direct a computer or other programmable apparatus to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

Referring now to FIGS. 4A and 4B, an example method is illustrated. In some embodiments, the example method detects a change in the resonant frequency of a porous media to determine if a blockage or potential blockage of the porous media exists.

The example method 400 of FIGS. 4A and 4B starts at step/operation 405. In some embodiments, steps/operations 410, 415, and 420 together illustrate a calibration or detection of the baseline resonant frequency. At step/operation 410, a processor (such as, but not limited to, the processing circuitry 205 of the gas diffusion sensor 100 described above in connection with FIG. 2) sends a signal to a vibration actuator (such as, but not limited to, a piezoelectric actuator), which is coupled to a resonator (such as, but not limited to, a tuning fork or tuning prong) to vibrate at each of a plurality of different frequencies, thereby also causing the coupled resonator to vibrate at those frequencies.

The range of specific frequencies and the number of frequencies (and therefore the spacing between each frequency) used may vary based at least on the specific structure and materials of the porous media. In some embodiments, advance testing is performed on each specific porous media design to determine the approximate range of frequencies in which the porous media's resonant frequency is likely to fall. While the resonant frequency of each porous media constructed may differ somewhat, for example due to manufacturing and materials variations, such advance testing may provide a frequency to use as a starting point for step/operation 410. In some embodiments, the vibration actuator and resonator are vibrated at a starting frequency (which, in some embodiments, may be determined through testing) and then alternatingly at frequencies successively lower and successively higher than the starting frequency until the resonant frequency is determined. In one example embodiment, the vibration actuator and resonator are vibrated starting at 900 Hertz ("Hz"), then at 895 Hz, then at 905 Hz, then at 890 Hz, then at 910 Hz, etc., until the resonant frequency is determined.

At step/operation 415, a processor (such as, but not limited to, the processing circuitry 205 of the gas diffusion sensor 100 described above in connection with FIG. 2) detects the displacement of the resonator as it vibrates at each of the plurality of different frequencies. In some embodiments, the displacement of the resonator is detected by measuring the capacitance between a conductive plate at the upper end of the resonator and one or two fixed-position electrodes, as described above.

Because the resonator is affixed to the porous media, the porous media also vibrates at each of the plurality of different frequencies. When the vibration occurs at the resonant frequency of the porous media, the magnitude of the vibration of the porous media (along with the resonator) will be significantly greater, thereby resulting in significantly greater displacement of the resonator. At step/operation 420, a processor (such as, but not limited to, the processing circuitry 205 of the gas diffusion sensor 100 described above in connection with FIG. 2) determines at which of the plurality of different frequencies the maximum displacement of the resonator occurred. This determined frequency is the baseline or calibrated resonant frequency of the porous media.

In some embodiments, steps/operations 425 and 430 together illustrate a detection of a change in the resonant frequency of the porous media which may indicate a blockage or potential blockage of the porous media. At step/operation 425, a processor (such as, but not limited to, the processing circuitry 205 of the gas diffusion sensor 100 described above in connection with FIG. 2) periodically sends a signal to the vibration actuator to vibrate at the baseline resonant frequency of the porous media (as determined at step/operation 420), thereby also causing the coupled resonator and the porous media to vibrate at that frequency, and determines the displacement of the resonator. In some embodiments, this step/operation is performed at random times. In some embodiments, this step/operation is performed regularly at predetermined intervals (e.g., every fifteen minutes or every hour). In some embodiments, the predetermined intervals are selected based on the expected environment in which the sensor is to be placed (e.g., shorter intervals in a dusty environment). In some embodiments, this step/operation is performed regularly at predetermined intervals that decrease over time from the time the porous media has been newly installed (e.g., every hour for the first week, every thirty minutes for the second week, every fifteen minutes for the third week, etc.).

At step/operation 430, a processor (such as, but not limited to, the processing circuitry 205 of the gas diffusion sensor 100 described above in connection with FIG. 2) compares the displacement of the resonator determined at step/operation 425 to the maximum displacement of the resonator determined at step/operation 420. If the displacement of the resonator determined at step/operation 425 is equal to the maximum displacement of the resonator determined at step/operation 420 (within a predetermined tolerance (e.g., ten percent)), this indicates that there is no (or little) change to the resonant frequency of the porous media and therefore no (or little) blockage of the porous media and steps/operations 425 and 430 are periodically repeated.

If the displacement of the resonator determined at step/operation 425 is not equal to the maximum displacement of the resonator determined at step/operation 420 (within a predetermined tolerance (e.g., ten percent)), this indicates that there a change to the resonant frequency of the porous media and therefore a potential blockage of the porous media.

In some embodiments, rather than performing steps/operations 425 and 430, detection of a change in the resonant frequency of the porous media may comprise periodically repeating steps/operations 410, 415, and 420 and comparing the resonant frequency determined at repeated step/operation 420 and comparing that to the resonant frequency determined at original step/operation 420.

In some embodiments, steps/operations 435-450 together illustrate a process for attempting to clear or partially clear a blockage of the porous media by determining the new resonant frequency of the porous media and vibrating the porous media at its new resonant frequency. In some embodiments, steps/operations 435-450 are very similar to steps/operations 410-420 except that the starting frequency at step/operation 435 is the baseline resonant frequency of the porous media.

At step/operation 435, a processor (such as, but not limited to, the processing circuitry 205 of the gas diffusion sensor 100 described above in connection with FIG. 2) sends a signal to the vibration actuator to vibrate at each of a plurality of different frequencies, thereby also causing the coupled resonator and the porous media to vibrate at those frequencies. As with steps/operations 410-420, the range of specific frequencies and the number of frequencies (and therefore the spacing between each frequency) used at steps/operations 435-450 may vary based at least on the specific structure and materials of the porous media. In some embodiments, the vibration actuator and resonator are vibrated at a starting frequency which is the baseline resonant frequency of the porous media and then alternatingly at frequencies successively lower and successively higher than the starting frequency until the new resonant frequency is determined.

At step/operation 440, a processor (such as, but not limited to, the processing circuitry 205 of the gas diffusion sensor 100 described above in connection with FIG. 2) detects the displacement of the resonator as it vibrates at each of the plurality of different frequencies. In some embodiments, the displacement of the resonator is detected by measuring the capacitance between a conductive plate at the upper end of the resonator and one or two fixed-position electrodes, as described above.

At step/operation 445, a processor (such as, but not limited to, the processing circuitry 205 of the gas diffusion sensor 100 described above in connection with FIG. 2) determines at which of the plurality of different frequencies the maximum displacement of the resonator occurred. This determined frequency is the new resonant frequency of the porous media.

At step/operation 450, a processor (such as, but not limited to, the processing circuitry 205 of the gas diffusion sensor 100 described above in connection with FIG. 2) sends a signal to the vibration actuator to vibrate at the new resonant frequency of the porous media (as determined at step/operation 445) for a predetermined length of time, thereby also causing the coupled resonator and the porous media to vibrate at that frequency. This vibration of the porous media, which is of an increased magnitude because the vibration is at the resonant frequency, is intended to dislodge some or all of the contaminants attached to the outer surface of the porous media and/or lodged in its pores to clear the porous media. The porous media may be vibrated for any suitable length of time, for example thirty or sixty seconds.

In some embodiments, steps/operations 455 and 460 together illustrate a process for determining if the attempt to clear or partially clear a blockage of the porous media was successful. At step/operation 455, a processor (such as, but not limited to, the processing circuitry 205 of the gas diffusion sensor 100 described above in connection with FIG. 2) sends a signal to the vibration actuator to vibrate at the baseline resonant frequency of the porous media (as determined at step/operation 420), thereby also causing the coupled resonator and the porous media to vibrate at that frequency, and determines the displacement of the resonator.

At step/operation 460, a processor (such as, but not limited to, the processing circuitry 205 of the gas diffusion sensor 100 described above in connection with FIG. 2) compares the displacement of the resonator determined at step/operation 455 to the maximum displacement of the resonator determined at step/operation 420. If the displacement of the resonator determined at step/operation 455 is equal to the maximum displacement of the resonator determined at step/operation 420 (within a predetermined tolerance (e.g., ten percent)), this indicates that the attempt to clear or partially clear a blockage of the porous media was successful. After such a successful clearing process, steps/operations 425 and 430 are periodically repeated.

If the displacement of the resonator determined at step/operation 455 is not equal to the maximum displacement of the resonator determined at step/operation 420 (within a predetermined tolerance (e.g., ten percent)), this indicates that the attempt to clear or partially clear a blockage of the porous media was unsuccessful. If the attempt to clear or partially clear a blockage of the porous media was unsuccessful, at step/operation 465, a processor (such as, but not limited to, the processing circuitry 205 of the gas diffusion sensor 100 described above in connection with FIG. 2) creates an alert notification that the porous media should be manually cleared or replaced.

In some embodiments, after manual clearing or replacement of the porous media, the process begins again at step/operation 410.

Additionally or alternatively to the clearing process described in steps/operations 455 and 460, in some embodiments a blockage of the porous media is attempted to be cleared by vibrating the resonator at a low frequency (for example, 165 Hz) for a predetermined period of time.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. An apparatus comprising at least one processor and at least one non-transitory memory comprising program code, wherein the at least one non-transitory memory and the program code are configured to, with the at least one processor, cause the apparatus to at least:

transmit a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies;

detect a plurality of vibration displacements of the resonator, each of the plurality of vibration displacements corresponding to a different one of the plurality of frequencies;

from the plurality of vibration displacements, determine a maximum vibration displacement of the resonator and an associated one of the plurality of frequencies at which the maximum vibration displacement occurs, thereby determining a resonant frequency of the porous media; and periodically determine if the resonant frequency of the porous media has changed by:

transmitting a resonance signal to the vibration actuator to cause the vibration actuator, and therefore the coupled resonator, to vibrate at the determined resonant frequency of the porous media;

detecting a verification vibration displacement of the resonator; and determining if the verification vibration displacement of the resonator is within a predetermined range of the maximum vibration displacement of the resonator.

2. The apparatus of claim 1, wherein the vibration actuator comprises a piezoelectric actuator or an electromagnetic actuator.

3. The apparatus of claim 1, wherein the resonator comprises one of a tuning prong or a tuning fork.

4. The apparatus of claim 1, wherein the porous media comprises porous frit.

5. The apparatus of claim 1, wherein the plurality of signals transmitted to the vibration actuator is a first plurality of signals;

wherein the plurality of vibration displacements is a first plurality of vibration displacements;

wherein the plurality of frequencies is a first plurality of frequencies;

wherein the resonant frequency of the porous media is a first resonant frequency;

wherein the resonance signal is a first resonance signal;

wherein the maximum vibration displacement is a first maximum vibration displacement; and wherein, if the verification vibration displacement of the resonator is determined to not be within the predetermined range of the first maximum vibration displacement of the resonator, the at least one non-transitory memory and the program code are configured to, with the at least one processor, cause the apparatus to:

transmit a second plurality of signals to the vibration actuator, each of the second plurality of signals causing the vibration actuator, and therefore the coupled resonator, to vibrate at a corresponding different one of a second plurality of frequencies;

detect a second plurality of vibration displacements of the resonator, each of the second plurality of vibration displacements corresponding to a different one of the second plurality of frequencies;

from the second plurality of vibration displacements, determine a second maximum vibration displacement of the resonator and an associated one of the second plurality of frequencies at which the second maximum vibration displacement occurs, thereby determining a second resonant frequency of the porous media; and transmit a second resonance signal to the vibration actuator to cause the vibration actuator, and therefore the coupled resonator, to vibrate at the second resonant frequency for a predetermined amount of time to attempt to dislodge any foreign matter on or in the porous media.

6. The apparatus of claim 5, wherein transmitting the second resonance signal to the vibration actuator causes the vibration actuator, and therefore the coupled resonator, to vibrate at a higher magnitude than vibrations caused by the first plurality of signals, the second plurality of signals, or the first resonance signal.

7. The apparatus of claim 5, wherein the verification vibration displacement is a first verification vibration displacement;

wherein, after transmitting the second resonance signal to the vibration actuator to cause the vibration actuator, and therefore the coupled resonator, to vibrate at the second resonant frequency for the predetermined amount of time, the at least one non-transitory memory and the program code are configured to, with the at least one processor, cause the apparatus to:

transmit the first resonance signal to the vibration actuator to cause the vibration actuator, and therefore the coupled resonator, to vibrate at the first resonant frequency of the porous media;

detect a second verification vibration displacement of the resonator; and determine if the second verification vibration displacement of the resonator is within the predetermined range of the first maximum vibration displacement of the resonator; and wherein, if the second verification vibration displacement of the resonator is determined to not be within the predetermined range of the first maximum vibration displacement of the resonator, the at least one non-transitory memory and the program code are configured to, with the at least one processor, cause the apparatus to provide an alert that manual clearing or replacement of the porous media is needed.

8. A computer-implemented method comprising:

transmitting a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies;

detecting a plurality of vibration displacements of the resonator, each of the plurality of vibration displacements corresponding to a different one of the plurality of frequencies;

from the plurality of vibration displacements, determining a maximum vibration displacement of the resonator and an associated one of the plurality of frequencies at which the maximum vibration displacement occurs, thereby determining a resonant frequency of the porous media; and periodically determining if the resonant frequency of the porous media has changed by:

transmitting a resonance signal to the vibration actuator to cause the vibration actuator, and therefore the coupled resonator, to vibrate at the determined resonant frequency of the porous media;

detecting a verification vibration displacement of the resonator; and determining if the verification vibration displacement of the resonator is within a predetermined range of the maximum vibration displacement of the resonator.

9. The computer-implemented method of claim 8, wherein the vibration actuator comprises a piezoelectric actuator or an electromagnetic actuator.

10. The computer-implemented method of claim 8, wherein the resonator comprises one of a tuning prong or a tuning fork.

11. The computer-implemented method of claim 8, wherein the porous media comprises porous frit.

12. The computer-implemented method of claim 8, wherein the plurality of signals transmitted to the vibration actuator is a first plurality of signals;

wherein the plurality of vibration displacements is a first plurality of vibration displacements;

wherein the plurality of frequencies is a first plurality of frequencies;

wherein the resonant frequency of the porous media is a first resonant frequency;

wherein the resonance signal is a first resonance signal;

wherein the maximum vibration displacement is a first maximum vibration displacement; and wherein, if the verification vibration displacement of the resonator is determined to not be within the predetermined range of the first maximum vibration displacement of the resonator, the computer-implemented method further comprises:

transmitting a second plurality of signals to the vibration actuator, each of the second plurality of signals causing the vibration actuator, and therefore the coupled resonator, to vibrate at a corresponding different one of a second plurality of frequencies;

detecting a second plurality of vibration displacements of the resonator, each of the second plurality of vibration displacements corresponding to a different one of the second plurality of frequencies;

from the second plurality of vibration displacements, determining a second maximum vibration displacement of the resonator and an associated one of the second plurality of frequencies at which the second maximum vibration displacement occurs, thereby determining a second resonant frequency of the porous media; and transmitting a second resonance signal to the vibration actuator to cause the vibration actuator, and therefore the coupled resonator, to vibrate at the second resonant frequency for a predetermined amount of time to attempt to dislodge any foreign matter on or in the porous media.

13. The computer-implemented method of claim 12, wherein transmitting the second resonance signal to the vibration actuator causes the vibration actuator, and therefore the coupled resonator, to vibrate at a higher magnitude than vibrations caused by the first plurality of signals, the second plurality of signals, or the first resonance signal.

14. The computer-implemented method of claim 12, wherein the verification vibration displacement is a first verification vibration displacement;

wherein, after transmitting the second resonance signal to the vibration actuator to cause the vibration actuator, and therefore the coupled resonator, to vibrate at the second resonant frequency for the predetermined amount of time, the computer-implemented method further comprises:

transmitting the first resonance signal to the vibration actuator to cause the vibration actuator, and therefore the coupled resonator, to vibrate at the first resonant frequency of the porous media;

detecting a second verification vibration displacement of the resonator; and determining if the second verification vibration displacement of the resonator is within the predetermined range of the first maximum vibration displacement of the resonator; and wherein, if the second verification vibration displacement of the resonator is determined to not be within the predetermined range of the first maximum vibration displacement of the resonator, the computer-implemented method further comprises providing an alert that manual clearing or replacement of the porous media is needed.

15. A computer program product comprising at least one non-transitory computer-readable storage medium having computer-readable program code portions stored therein, the computer-readable program code portions comprising an executable portion configured to:

transmit a plurality of signals to a vibration actuator coupled to a resonator, the resonator being affixed to a porous media of a diffusion sensor, each of the plurality of signals causing the vibration actuator, and therefore the coupled resonator, to vibrate at a corresponding different one of a plurality of frequencies;

detect a plurality of vibration displacements of the resonator, each of the plurality of vibration displacements corresponding to a different one of the plurality of frequencies;

from the plurality of vibration displacements, determine a maximum vibration displacement of the resonator and an associated one of the plurality of frequencies at which the maximum vibration displacement occurs, thereby determining a resonant frequency of the porous media; and periodically determine if the resonant frequency of the porous media has changed by:

transmitting a resonance signal to the vibration actuator to cause the vibration actuator, and therefore the coupled resonator, to vibrate at the determined resonant frequency of the porous media;

detecting a verification vibration displacement of the resonator; and determining if the verification vibration displacement of the resonator is within a predetermined range of the maximum vibration displacement of the resonator.

16. The computer program product of claim 15, wherein the vibration actuator comprises a piezoelectric actuator or an electromagnetic actuator.

17. The computer program product of claim 15, wherein the resonator comprises one of a tuning prong or a tuning fork.

18. The computer program product of claim 15, wherein the plurality of signals transmitted to the vibration actuator is a first plurality of signals;

wherein the plurality of vibration displacements is a first plurality of vibration displacements;

wherein the plurality of frequencies is a first plurality of frequencies;

wherein the resonant frequency of the porous media is a first resonant frequency;

wherein the resonance signal is a first resonance signal;

wherein the maximum vibration displacement is a first maximum vibration displacement; and wherein, if the verification vibration displacement of the resonator is determined to not be within the predetermined range of the first maximum vibration displacement of the resonator, the computer-readable program code portions comprise the executable portion configured to:

transmit a second plurality of signals to the vibration actuator, each of the second plurality of signals causing the vibration actuator, and therefore the coupled resonator, to vibrate at a corresponding different one of a second plurality of frequencies;

detect a second plurality of vibration displacements of the resonator, each of the second plurality of vibration displacements corresponding to a different one of the second plurality of frequencies;

from the second plurality of vibration displacements, determine a second maximum vibration displacement of the resonator and an associated one of the second plurality of frequencies at which the second maximum vibration displacement occurs, thereby determining a second resonant frequency of the porous media; and transmit a second resonance signal to the vibration actuator to cause the vibration actuator, and therefore the coupled resonator, to vibrate at the second resonant frequency for a predetermined amount of time to attempt to dislodge any foreign matter on or in the porous media.

19. The computer program product of claim 18, wherein transmitting the second resonance signal to the vibration actuator causes the vibration actuator, and therefore the coupled resonator, to vibrate at a higher magnitude than vibrations caused by the first plurality of signals, the second plurality of signals, or the first resonance signal.

20. The computer program product of claim 18, wherein the verification vibration displacement is a first verification vibration displacement;

wherein, after transmitting the second resonance signal to the vibration actuator to cause the vibration actuator, and therefore the coupled resonator, to vibrate at the second resonant frequency for the predetermined amount of time, the computer-readable program code portions comprise the executable portion configured to:

transmit the first resonance signal to the vibration actuator to cause the vibration actuator, and therefore the coupled resonator, to vibrate at the first resonant frequency of the porous media;

detect a second verification vibration displacement of the resonator; and determine if the second verification vibration displacement of the resonator is within the predetermined range of the first maximum vibration displacement of the resonator; and wherein, if the second verification vibration displacement of the resonator is determined to not be within the predetermined range of the first maximum vibration displacement of the resonator, the computer-readable program code portions comprise the executable portion configured to provide an alert that manual clearing or replacement of the porous media is needed.

* * * * *